United States Patent
Tanaka et al.

(10) Patent No.: US 12,285,526 B2
(45) Date of Patent: Apr. 29, 2025

(54) NANOPARTICLE COMPOSITION WITH REDUCED CONTAMINANT AND PRODUCTION METHOD THEREOF

(71) Applicants: Shionogi & Co., Ltd., Osaka (JP); HIROSHIMA METAL & MACHINERY CO., LTD., Tokyo (JP)

(72) Inventors: Hironori Tanaka, Hyogo (JP); Yuya Ochii, Hyogo (JP); Tetsuharu Ibaraki, Hiroshima (JP)

(73) Assignees: SHIONOGI & CO., LTD., Osaka (JP); HIROSHIMA METAL & MACHINERY CO., LTD., Tokyo (JP)

( * ) Notice: Subject to any disclaimer, the term of this patent is extended or adjusted under 35 U.S.C. 154(b) by 799 days.

(21) Appl. No.: 17/434,883

(22) PCT Filed: Feb. 28, 2020

(86) PCT No.: PCT/JP2020/008441
§ 371 (c)(1),
(2) Date: Aug. 30, 2021

(87) PCT Pub. No.: WO2020/179701
PCT Pub. Date: Sep. 10, 2020

(65) Prior Publication Data
US 2022/0160634 A1 May 26, 2022

(30) Foreign Application Priority Data
Mar. 1, 2019 (JP) .................. 2019-037358

(51) Int. Cl.
A61K 9/14 (2006.01)
B02C 17/20 (2006.01)
(Continued)

(52) U.S. Cl.
CPC ............... *A61K 9/14* (2013.01); *B02C 17/20* (2013.01); *B82Y 5/00* (2013.01); *B82Y 40/00* (2013.01)

(58) Field of Classification Search
CPC .......... A61K 9/14; A61K 9/146; A61K 9/145; B02C 17/20; B02C 17/00; B02C 17/16; B82Y 5/00; B82Y 40/00
See application file for complete search history.

(56) References Cited

U.S. PATENT DOCUMENTS

| 5,518,187 A | 5/1996 | Bruno et al. |
| 6,582,285 B2 | 6/2003 | Czekai et al. |

(Continued)

FOREIGN PATENT DOCUMENTS

| EP | 0 600 528 | 6/1994 |
| EP | 1 923 051 | 5/2008 |

(Continued)

OTHER PUBLICATIONS

Tanaka et al, "Development of Novel Bead Milling Technology with Less Metal Contamination by pH Optimization of the Suspension Medium", Chem. Pharm. Bull., 2021, vol. 69, No. 1, pp. 81-85. (Year: 2021).*

(Continued)

*Primary Examiner* — Benjamin J Packard
*Assistant Examiner* — Joshua A Atkinson
(74) *Attorney, Agent, or Firm* — Wenderoth, Lind & Ponack, L.L.P.

(57) ABSTRACT

A method for the production of the present disclosure comprises: a) a step of agitating a mixture containing a material to be ground, beads and a dispersion medium in a bead mill; and b) a step of adjusting the pH of the mixture. This method reduces a contamination caused by grinding process using a bead mill.

17 Claims, 3 Drawing Sheets

(51) Int. Cl.
    *B82Y 5/00*         (2011.01)
    *B82Y 40/00*        (2011.01)

(56) References Cited

U.S. PATENT DOCUMENTS

| | | | | |
|---|---|---|---|---|
| 9,044,758 | B2 * | 6/2015 | Niwa | B02C 17/16 |
| 2008/0213383 | A1 * | 9/2008 | Yamaguchi | A61K 9/10 |
| | | | | 424/499 |
| 2010/0074827 | A1 * | 3/2010 | Rainer | C04B 35/486 |
| | | | | 423/430 |

FOREIGN PATENT DOCUMENTS

| | | |
|---|---|---|
| JP | 5-294610 | 11/1993 |
| JP | 2007-70133 | 3/2007 |
| WO | 93/25190 | 12/1993 |
| WO | 02/30572 | 4/2002 |
| WO | 2010/121323 | 10/2010 |
| WO | 2014/009436 | 1/2014 |
| WO | 2019/208725 | 10/2019 |
| WO | 2021/033633 | 2/2021 |

OTHER PUBLICATIONS

JP 2007070133 A, English translation of prior submitted foreign patent. (Year: 2007).*

Extended European Search Report dated Dec. 22, 2022 issued in European Application No. 20766094.5.

Nakach, Mostafa et al., "Engineering of nano-crystalline drug suspensions: Employing a physico-chemistry based stabilizer selection methodology or approach", International Journal of Pharmaceutics, 2014, vol. 476, pp. 277-288.

Inkyo, Mitsugi et al., "Experimental investigation of nanoparticle dispersion by beads milling with centrifugal bead separation", Journal of Colloid and Interface Science, 2006, vol. 304, pp. 535-540.

Funahashi, Isao et al., "Novel contamination-free wet milling technique using ice beads for poorly water-soluble compounds", International Journal of Pharmaceutics, 2019, vol. 563, pp. 413-425.

Tahara, Takashi et al., "Low-energy bead milling dispersions of rod-type titania nanoparticles and their optical properties", Advanced Powder Technology, 2014, vol. 25, Issue 5, pp. 1492-1499.

Moribe, Kunikazu et al., "Nanocrystal formulation of poorly water-soluble drug", Drug Delivery System, 2015, vol. 30, No. 2, pp. 92-99, with English Abstract.

International Search Report issued May 19, 2020 in International (PCT) Application No. PCT/JP2020/008441.

Translation of International Preliminary Report on Patentability and Written Opinion of the International Searching Authority dated May 19, 2020 in International (PCT) Application No. PCT/JP2020/008441.

* cited by examiner

NANOPARTICLE COMPOSITION WITH REDUCED CONTAMINANT AND PRODUCTION METHOD THEREOF

TECHNICAL FIELD

The present disclosure relates to a method for refinement of solid particles using a bead mill and also to particles refined by said method.

BACKGROUND ART

Wet-grinding using a grinding machine such as a bead mill was known as a means for refining solid particles. Wet-grinding using a bead mill has a high ability of grinding particles, and therefore, it is possible to finely grind particles to a particle size on the order of submicron.

The bead mill is a machine that gives a large amount of kinetic energy to beads by agitating a grinding medium (beads) with an agitator in a grinding chamber, and makes the particles finer by collision force and shearing force of the beads. Therefore, in wet-grinding using a bead mill, a contamination of the product due to wear of the grinding medium (beads) and mill members (agitator, etc.) may occur.

Especially in the fields of high-purity electronic component raw materials and pharmaceuticals, even a small amount of impurities may have adverse effects such as deterioration of product performance and health hazards. Therefore, such contamination must be avoided.

Patent Document 1 describes that agitating surface inside the agitator is made a smooth and continuous surface without seams or recesses to prevent accumulation of contaminants on the agitating surface.

Patent Document 2 describes that fine particles of a drug can be produced with less contamination by grinding the drug in the presence of a grinding medium containing beads made of a polymer resin or beads coated with a polymer resin.

Patent Document 3 describes that particles of a non-steroidal anti-inflammatory drug (NSAID) are dispersed in a liquid dispersion medium and then wet-ground in the presence of a hard grinding medium under acidic conditions of pH 2 to 6 to obtain particles having an average particle size less than about 400 nm.

Non-Patent Document 1 describes that milling was performed efficiently in the presence of sodium lauryl sulfate and polyvinylpyrrolidone in the dispersion medium.

PRIOR ART DOCUMENT

Patent Document

[Patent Document 1] U.S. Pat. No. 6,582,285
[Patent Document 2] JP 2003-175341 A
[Patent Document 3] JP H8-501073 A

Non-Patent Document

[Non-Patent Document 1] Engineering of nano-crystalline drug suspensions (Archive ouverte HAL)

SUMMARY OF INVENTION

Problem to be Solved by the Invention

The object of the present disclosure is to reduce contamination caused by a grinding process using a bead mill.

Means for Solving the Problem

As a result of investigating various factors affecting contamination in a grinding process using a bead mill, the inventors have found that the pH of the slurry during grinding process has a great significance. Thus, the present disclosure is based on the discovery that the contamination caused by grinding process can be reduced by controlling the pH of the slurry of the material to be ground during the grinding process by bead mill.

The present description discloses the followings:
(1) A method for the production of fine particles via a grinding process using a bead mill,
wherein the method comprises:
 a) a step of agitating a mixture containing a material to be ground, beads and a dispersion medium in the bead mill; and
 b) a step of adjusting the pH of the mixture.
(2) The method according to (1) wherein the dispersion medium contains one or more selected from the group consisting of sodium linear alkylbenzene sulfonate, monoalkyl phosphate, sodium lauryl sulfate, cellulose polymer and vinyl polymer.
(3) The method according to (1) wherein the dispersion medium contains polyvinylpyrrolidone.
(4) The method according to (1) wherein the dispersion medium contains sodium lauryl sulfate.
(5) The method according to (1) wherein the dispersion medium contains polyvinylpyrrolidone and sodium lauryl sulfate.
(6) The method according to any one of (1) to (5) wherein the step b) of adjusting the pH is a step of adjusting the pH by adding an acidic substance or a basic substance.
(7) The method according to any one of (1) to (6) wherein the impurities caused by the grinding process are reduced as compared with those before adjusting the pH.
(8) The method according to any one of (1) to (7) wherein impurities are derived from the beads and/or the bead mill.
(9) The method according to any one of (1) to (8) wherein the amount of impurities is less than 50 ppm with respect to the weight of the material to be ground.
(10) The method according to any one of (1) to (9) wherein the beads are zirconia beads.
(11) The method according to any one of (1) to (10) wherein the beads comprise zirconium, yttrium and aluminum.
(12) The method according to any one of (1) to (11) wherein impurities are one or more selected from the group consisting of zirconium, yttrium and aluminum.
(13) The method according to any one of (1) to (12) wherein the step b) is a step of adjusting the pH of the mixture to 6.5 to 9.
(14) A method for the production of fine particles via a grinding process using a bead mill, wherein the method comprises mixing a material to be ground, beads and a dispersion medium and agitating the mixture at a pH of 6.5 to 9 and wherein the amount of impurities is less than 50 ppm with respect to the weight of the material to be ground.
(15) The method according to any one of (1) to (14), wherein the fine particles are microparticles.

(16) The method according to any one of (1) to (14), wherein the fine particles are nanoparticles.
(17) The method according to any one of (1) to (16), wherein the material to be ground is a pharmaceutical compound.
(18) Fine particles obtained by the method according to any one of (1) to (17).
(19) The fine particles according to (18), which are microparticles.
(20) The fine particles according to (18), which are nanoparticles.
(21) The fine particles according to any one of (18) to (20), which comprises a pharmaceutical compound.
(22) The fine particles according to any one of (18) to (21), wherein the amount of one or more impurities selected from the group consisting of zirconium, yttrium and aluminum is 0.0001 ppm or more and less than 50 ppm.
(23) A pharmaceutical composition comprising the fine particles according to any one of (17) to (22).
(24) A method for reducing impurities caused by a grinding process using a bead mill,
wherein the method comprises:
   a) a step of agitating a mixture containing a material to be ground, beads and a dispersion medium; and
   b) a step of adjusting the pH of the mixture.
(25) A method for reducing impurities caused by a grinding process using a bead mill,
wherein the method comprises:
   a) a step of mixing a material to be ground, beads and dispersion medium;
   b) a step of adjusting the pH of the mixture obtained in step a); and
   c) a step of agitating the mixture in the bead mill.
(26) The method according to (25), wherein the step b) is a step of adjusting the pH of the mixture obtained in the step a) to 6.5 to 9.
(27) The method according to (25) or (26), wherein the amount of impurities is 0.0001 ppm or more and less than 50 ppm with respect to the weight of the material to be ground.

Effect of the Invention

The method of the present disclosure reduces the contamination caused by a grinding process in a bead mill.

EMBODIMENTS FOR CARRYING OUT THE INVENTION

In one embodiment of the present disclosure, a method for the production of fine particles via a grinding process using a bead mill is provided.

The term "fine particles" (also herein referred to as "refined particles") as used herein is solid particles with an average particle size of 1000 µm or less, which may have any shape, not limited to a spherical shape, obtained by grinding techniques using a bead mill (also herein referred to as "grinding process").

In the present disclosure, the average particle size of particles is expressed as a volume-based median diameter (D50). A skilled person can determine the median diameter according to conventional methods.

As used herein, the term "microparticles" means fine particles as described above having an average particle size on the micron order, for example, about 1 µm to about 1000 µm, about 1 µm to about 100 µm, about 1 µm to about 10 µm, about 10 µm to about 1000 µm, about 100 µm to about 1000 µm, about 10 µm to about 50 µm, about 50 µm to about 100 µm, about 1 µm to about 50 µm, about 1 µm to about 30 µm, and about 1 µm to about 10 µm.

As used herein, the term "nanoparticles" means fine particles as described above having an average particle size on the nano order, for example, about 1 nm to about 1000 nm, for example, about 1 nm to about 100 nm, about 1 nm to about 10 nm, about 10 nm to about 1000 nm, about 100 nm to about 1000 nm, about 10 nm to about 50 nm, about 50 nm to about 100 nm, about 1 nm to about 50 nm, about 1 nm to about 30 nm, and about 1 nm to about 10 nm.

As used herein, the term "material to be ground" means a solid substance to be refined by the grinding process of the present disclosure, and the material is usually powder or granular material of a solid substance. The particles size of the material before grinding is not limited so long as it is in a range capable of refined into nanoparticles or microparticles using a bead mill. The particle size of the material to be ground by the grinding process of the present disclosure is, for example, in the range of 1 µm to 100 µm, 1 µm to 75 µm, 1 µm to 50 µm, 1 µm to 25 µm, 1 µm to 10 µm, and 1 µm to 5 µm.

The material to be ground used in the grinding process of the present disclosure may be any solid substance as used in various technical fields, including electronic component materials such as dielectrics, piezoelectrics and magnetic materials, phosphors, electrode materials for batteries, pigments, paints, raw materials for fine ceramics, abrasives and pharmaceuticals, agrichemicals, powdered foods, and the like. For example, examples of the material to be ground used in the field of pharmaceuticals include pharmaceutical compounds that are active ingredients of pharmaceuticals, and may be crystalline or amorphous. Since the material to be ground is wet ground, it should be insoluble in water or poorly soluble in water.

In one embodiment, the grinding process of the present disclosure comprises:
   a) a step of agitating a mixture containing a material to be ground, beads and dispersion medium; and
   b) a step of adjusting the pH of the mixture.

The beads used in the grinding process of the present disclosure are not limited so long as they are usually used in a grinding technique using a bead mill.

A skilled person can select the material and the particle size of the beads, taking into consideration of various factors, including the spec of the bead mill, the properties of the material to be ground (for example, hardness, density and size of the particles, etc.), the target particle size of the fine particles after grinding, and the viscosity of slurry.

Examples of the material of the beads used in the bead mill include, but are not limited to, glass, alumina, zircon (zirconia-silica ceramics), zirconia and steel. In particular, zirconia is preferable as a material of the beads because it has a high hardness and tends to have less debris associated with bead deterioration.

The particle size of the beads may be, but is not limited to, the range of 0.03 mm to 1.0 mm, 0.1 mm to 1.0 mm, 0.1 mm to 0.8 mm, and 0.1 mm to 0.5 mm.

The dispersion medium used in the grinding process of the present disclosure is not limited so long as it is a liquid medium in which the material to be ground is essentially insoluble. A skilled person could appropriately select such dispersion medium depending on the properties of the material to be ground. Examples include water and various organic solvents (e.g., alcohols such as methanol, ethanol, isopropanol and butanol, ketones such as acetone, methyl ethyl ketone, methyl propyl ketone and methyl isobutyl ketone, ethers such as isopropyl ether and methyl cellosolve, glycol esters such as ethylene glycol, propylene glycol monomethyl ether acetate and ethylene glycol monoethyl ether acetate, esters such as ethyl acetate, halogenated hydrocarbons such as methylene chloride and trichloroethane, non-aromatic hydrocarbons such as cyclohexane, aromatic hydrocarbons such as toluene, and linear hydrocarbons such as normal hexane, and the like).

The amount of the dispersion medium is not limited so long as it is sufficient to disperse the material to be ground and make a slurry having a viscosity which is appropriate in the grinding process using a bead mill. A skilled person could appropriately select the amount of the dispersion medium depending on the properties of the material and the medium.

Agitation of the mixture in the step a) may be carried out according to a conventional procedure in a grinding technique using a bead mill. That is, the mixture is agitated with an agitator in a grinding chamber of a bead mill under appropriate operating conditions of the bead mill.

Adjustment of the pH in the step b) may be carried out after or before the step a). When adjusting the pH before the step a), for example, 1) the pH of a slurry in which a material to be ground has been dispersed in a dispersion medium is adjusted and then beads are added to prepare a mixture for the step a) or 2) beads and a material to be ground are added and dispersed in a dispersion medium and then the pH of the slurry is adjusted to obtain a mixture for the step a). The pH can be adjusted by adding an acidic, a basic or a neutral substance, particularly an acidic substance or a basic substance. For example, the pH can be adjusted by adding an acidic, basic or neutral solution, especially an acidic or basic solution, which may be buffered or not. Thus, by adding such solution to a dispersion medium having a pH on acidic side or basic side, the pH can be adjusted to that capable to reduce metallic foreign substances, whereby the metallic foreign substances can be reduced. The acidic substance as used herein means a compound having a hydrogen atom which becomes a hydrogen ion ($H^+$) when dissolved and ionized in water, and in a broad sense, it is a substance that gives a hydrogen ion to another substance. A basic substance is a compound having a hydroxyl group which becomes a hydroxide ion ($OH^-$) when dissolved and ionized in water, and in a broad sense, it is a substance that accepts hydrogen ions. Examples of the solution used for adjusting the pH in the present disclosure include, but are not limited to, aqueous solutions of acetic acid, hydrochloric acid, a citrate buffer, a carbonate buffer, a phosphate buffer, sodium hydroxide, potassium hydroxide and calcium hydroxide and ammonia solution. A skilled person could select appropriately the type of solution and the pH thereof, concentration and volume used for pH adjustment, taking into consideration of various factors such as the target pH, the material to be ground, the dispersion medium and the properties of other components in the slurry.

In one embodiment using zirconia beads, the pH in the above step b) can be adjusted to the range of 6 to 9, for example, the range of 6 to 8.5, the range of 6 to 8, the range of 6.5 to 9, the range of 6.5 to 8.5, the range of 6.5 to 8, the range of 7.5 to 9, the range of 7.5 to 8.5, and the range of 7.5 to 8.

The grinding process of the present disclosure can be carried out using a commercially available bead mill machine. The spec and type of the bead mill machine are not limited. The shape of the agitator assembled in the bead mill machine is not limited, and may be any of, for example, a disc type, a pin type, a single rotor type, and the like. The grinding chamber may be of either a vertical type or a horizontal type. Also, the mode of operation of the bead mill is not limited, and may be any of a circulation method, a pass method, a batch method, and the like.

A skilled person could appropriately select the amount of beads to be used, taking into consideration of various factors such as the spec of the bead mill (for example, the capacity of the grinding chamber), the operating conditions and the viscosity of the slurry.

The total amount of the mixture containing the material to be ground, the beads and the dispersion medium to be charged into the bead mill can be appropriately selected by a skilled person depending on the spec of the bead mill (for example, the capacity of the grinding chamber), the operating conditions, and the like.

In general, the volume of beads can be appropriately selected within the range of 10 to 90%, for example, 25 to 90%, 50 to 90%, and 60 to 90% of the capacity of the grinding chamber.

The operating conditions of the bead mill machine (e.g., agitator peripheral speed, cooling temperature, residence time (processing time), etc.) are determined according to conventional procedures, taking into consideration of the spec of the bead mill and various factors (property of the material to be ground, type of dispersion medium, viscosity of the slurry, filling ratio of beads in the mill, type of beads, particle size of fine particles obtained after grinding, grinding efficiency, etc.).

In the grinding process of the present disclosure, additives can be added to the slurry as needed. For example, a dispersant may be added to the slurry for the purpose of improving the dispersibility of the materials in the slurry, preventing aggregation, or stabilizing the dispersion state.

The dispersant can be appropriately selected, taking into consideration of various factors such as properties of the material to be ground and the dispersion medium, spec of the bead mill and operating conditions. Example of such dispersant include, but are not limited to, surfactants such as carboxylate (fatty acid salt, etc.), sulfonates (sodium liner alkylbenzene sulfonate, etc.), phosphates (monoalkyl phosphate, etc.), sulfate ester salts (sodium lauryl sulfate, etc.) and the like, and polymer compounds such as hydroxypropyl cellulose (HPC), hypromerose (hydroxypropyl methyl cellulose (HPMC)), methyl cellulose (MC), polyvinylpyrrolidone (PVP) and the like, especially water-soluble polymer compounds. Preferred are sodium lauryl sulfate and polyvinylpyrrolidone. The amount of the dispersant can be appropriately selected by a skilled person according to conventional procedures. In case that the dispersant is a surfactant, the amount thereof is, for example, 0.01 to 10.0% by weight, preferably 0.05 to 7.5% by weight, more preferably 0.1 to 5.0% by weight, with respect to the total amount of the slurry. In case that the dispersant is a polymer compound, the amount thereof is, for example, 0.1 to 20.0% by weight, preferably 0.25 to 15.0% by weight, more preferably 0.5 to 10.0% by weight, with respect to the total amount of the slurry. If a dispersant is not used in dispersion medium, it is possible that the material to be ground is not sufficiently dispersed in the dispersion medium or the grinding efficiency may be decreased. Also, as a result of dissolving or suspending a dispersant and/or a polymer compound in the dispersion medium, the pH of the dispersion medium may become a pH at which the amount of metal foreign substances cannot be reduced. In such case, the pH can be adjusted to a pH capable of reducing the metal foreign substances, using a solution for adjusting the pH, such as aqueous acetic acid solution, aqueous hydrochloric acid solution, citrate buffer solution, carbonate buffer solution, phosphate buffer solution, sodium hydroxide solution, potassium hydroxide solution, calcium hydroxide solution and aqueous ammonia solution, and the like.

The particles ground by the grinding process of the present disclosure are discharged from the bead mill as a slurry containing fine particles, after the separation of the beads by a separator in the bead mill. The spec and type of the separator are not limited and should depend on the bead mill used.

The slurry discharged from the bead mill may be used as it is in the form of a slurry containing fine particles, or the slurry is dried to remove a dispersion medium by conventional procedure to obtain a powder containing fine particles.

As used herein, the term "contamination" means that impurities occur during the grinding process by bead mill and said impurities are ingredients derived from the material of the components of bead mill (e.g., grinding chambers, stirrers, etc.) or ingredients derived from the material of the beads. Such impurities occur due to the wear of components of the bead mill and the beads during the grinding process.

In one embodiment, the amount of impurities by contamination due to the grinding process of the present disclosure is, for example, 0.0001 ppm or more and less than 50 ppm, 0.0001 ppm or more and less than 40 ppm, 0.0001 ppm or more and less than 30 ppm, 0.0001 ppm or more and less than 20 ppm, 0.0001 ppm or more and less than 10 ppm, with respect to the weight of the obtained fine particles.

In one embodiment, the impurities due to the grinding process of the present disclosure are derived from the beads.

In one embodiment using zirconia beads, the impurity is one or more of the ingredients composing the zirconia beads (e.g., zirconium, yttrium and aluminum).

In one embodiment, the impurities due to the grinding process of the present disclosure are derived from the material of the components of bead mill, and examples include elements composing stainless steel such as iron, molybdenum, chromium and nickel.

In a further embodiment of the present disclosure, the fine particles obtained by the method of the present disclosure are provided.

In one embodiment, the fine particles of the present disclosure are microparticles. In another embodiment, the fine particles of the present disclosure are nanoparticles.

In one embodiment, the fine particles of the present disclosure are nanoparticles comprising a pharmaceutical compound.

The form of the fine particles obtained by the method of the present disclosure is not limited. The fine particles may be in the form of slurry composition as obtained after the grinding process of the present disclosure, or the slurry composition may be mixed with an additive or dried and powdered. For removing foreign materials such as beads, the slurry can be filtered through a fine wet-sieve to remove the foreign materials, or the slurry may be centrifuged to separate and remove metal foreign substances (bead contamination).

Another embodiment of the present disclosure provides a composition or material comprising the fine particles obtained by the method of the present disclosure is provided. Examples of such composition and material include electronic component materials such as dielectrics, piezoelectrics and magnetic materials, phosphors, electrode materials for batteries, pigments, paints, raw materials for fine ceramics, abrasives and pharmaceuticals, agrichemicals, powdered foods, and the like.

Further embodiment of the present disclosure provides a pharmaceutical composition comprising the fine particles obtained by the method of the present disclosure is provided.

The pharmaceutical composition of the present disclosure can be obtained as a final product via several steps conventionally used in the pharmaceutical industry (e.g., granulation, tableting, coating, etc.), as appropriately depending on the dosage form of interest, using the fine particles obtained by the method of the present disclosure.

The following examples illustrate the disclosure in more detail and should not be construed as limiting its scope in any way.

EXAMPLES

Example 1

Phenitoin (Shizuoka Caffein Co., Ltd.) (7.5 g, 5 w/w %) as a drug, polyvinylpyrrolidone (PVP K-25, BASF Japan Ltd.) (4.5 g, 3 w/w %) as a polymer compound, sodium lauryl sulfate (Cognis Japan Ltd.) (0.375 g, 0.25 w/w %) as a surfactant were dispersed in 137.6 g of purified water to prepare a slurry. The pH of the slurry was 3.88. The pH was adjusted by adding 1N aqueous sodium hydroxide solution to this slurry, and samples having various pH (pH 6.07, 6.68, 7.36, 8.14, 8.96, 10.37) were prepared.

Each sample (100 g) and beads (217.3 g, filling ratio 70%) were charged into Dyno-mill Research Lab (manufactured by WAB), and the grinding process by the bead mill was carried out for 120 minutes (disc peripheral speed: 4 m/s, temperature: 20° C., fluid speed: 45 g/min). The beads used for the grinding process were YTZ ball (zirconia beads manufactured by Nikkato Corporation, with diameter of 0.5 mm). As used herein, the term "filling ratio" refers to the ratio (in percentage) of the true volume to the bulk volume of the beads, and hereinafter the same is applied.

The particle size of the drug particles after the grinding process was nano-order of less than 1 μm ($D_{50}$ value). The particle size was determined using Microtrac UPA 150 M (MicrotracBEL Corp.).

Measurement Conditions:
  Particle refractive index: 1.61
  Set Zero: 60 seconds
  Measurement time: 60 seconds
  Number of measurements: 2 times
  Shape: non-spherical
  Solvent refractive index: 1.333

The sample after the grinding process (0.5 g) was weighed in a metal-free container and added with internal standard substance (Co) and a mixed solution of $NMP/HCl/HNO_3$ (90:5:5), and dissolved by ultrasonic irradiation. The sample solution was subjected to inductively coupled plasma mass spectrometry (ICP-MS) (iCAPQ™, Thermo Fisher Scientific K.K.) to determine the amounts of the ingredients derived from beads (zirconium, yttrium and aluminum) (weight ppm/API, weight ppm of the drug in the sample).

Figure 1:
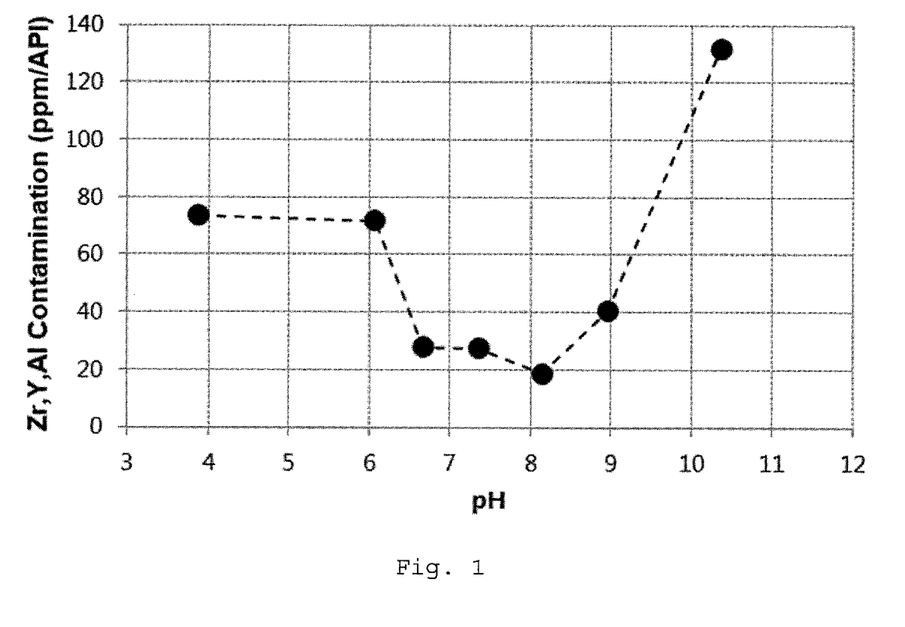
FIG. 1 shows beads-derived contamination in the sample of fine particles obtained in Example 1. The horizontal axis indicates the pH of the slurry during the grinding process. The vertical axis indicates the total amount of the elements derived from the beads (zirconia (Zr), yttrium (Y) and aluminum (Al)) in the sample (ppm/API: weight ppm with respect to drug fine particles).

Measurement Conditions:
  Elements to be measured: Zr (m/z=90), Y (m/z=89), Al (m/z=27)
  Nebulizer: Coaxial nebulizer
  Spray chamber: Cyclone type
  Spray chamber temperature: constant around 3° C.
  Injector inner diameter: 1.0 mm
  Sample introduction: Natural suction
  High frequency power: 1550 W
  Cooling gas flow rate: 14 L/min
  Auxiliary gas flow rate: 0.8 L/min
  Measurement mode: KED
  Collision gas: helium
  Additive gas: oxygen
  Perista pump rotation speed: 20 rpm
  Integration time: 0.1 seconds
  Accumulation number: 3 times The results are shown in FIG. 1. As shown in FIG. 1, the grinding process was carried out with adjusting the pH of the slurry to 6.68 to 8.14 and, the contamination by the ingredients derived from beads (zirconium, yttrium and aluminum) was significantly reduced.

Test Example 1: Effect of pH on the Elution of Ingredients Derived from Beads

Phenytoin (Shizuoka Caffein Co., Ltd.) (2.5 g, 5 w/w %) as a drug, polyvinylpyrrolidone (PVP K-25, BASF Japan Ltd.) (1.5 g, 3 w/w %) as a polymer compound, sodium lauryl sulfate (Cognis Japan Ltd.) (0.125 g, 0.25 w/w %) as a surfactant were dispersed in 45.88 g of purified water to prepare a slurry. The pH of this slurry was measured and found to be 3.88. The pH was adjusted to 6.17 by adding 1N NaOH to this slurry (45 mL).

YTZ ball (0.925 g, YTZ-0.5, manufactured by Nikkato Corporation, with diameter of 0.5 mm) was weighed in a falcon tube, and the slurry (5 mL) was added. The mixture was allowed to stand at 25° C. As a control, the slurry (pH 3.88) was used without pH adjustment.

After soaking for a predetermined time (1440 minutes, 2880 minutes), the supernatant was collected and subjected to inductively coupled plasma mass spectrometer (iCAPQ™, Thermo Fisher Scientific K.K.) to determine the amounts of zirconium, yttrium and aluminum (weight ppm/API), in the same manner as described in Example 1.

Figure 2:
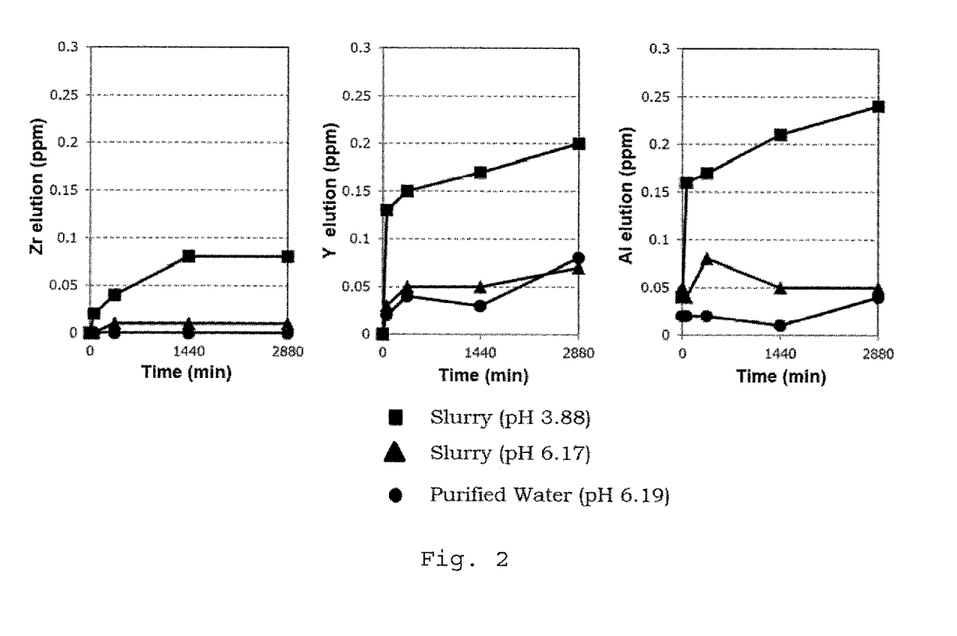
FIG. 2 shows the effect of pH on the elution of ingredients derived from beads in Test Example 1. The horizontal axis indicates the soaking time. The vertical axis indicates the amount of the elements derived from the beads in the sample (zirconia (Zr), yttrium (Y) and aluminum (Al)).

The results are shown in FIG. 2. As shown in FIG. 2, adjusting the pH of the slurry reduced the elution of the ingredients derived from beads.

Test Example 2: Effect of pH on the Grinding Efficiency

The pH of the slurry (pH 3.88) prepared in Test Example 1 was adjusted with 1N aqueous sodium hydroxide solution to prepare slurries having different pH values (pH 6.68, 7.36 and 8.14). As a control, the slurry (pH 3.88) prepared in Test Example 1 was used as it was without adjusting the pH.

Each slurry (100 g) and beads (217.3 g, filling ratio 70%) were charged into Dyno-mill Research Lab (manufactured by WAB), and the grinding process by the bead mill was carried out. The beads used for the grinding process were YTZ ball (zirconia beads manufactured by Nikkato Corporation, diameter of 0.5 mm).

Sampling was carried out at a predetermined time during the grinding process. The particle size of the drug particles in the sample was measured in the same manner as described in Example 1, and the $D_{50}$ value was calculated. The results are shown in FIG. 3.

Figure 3:
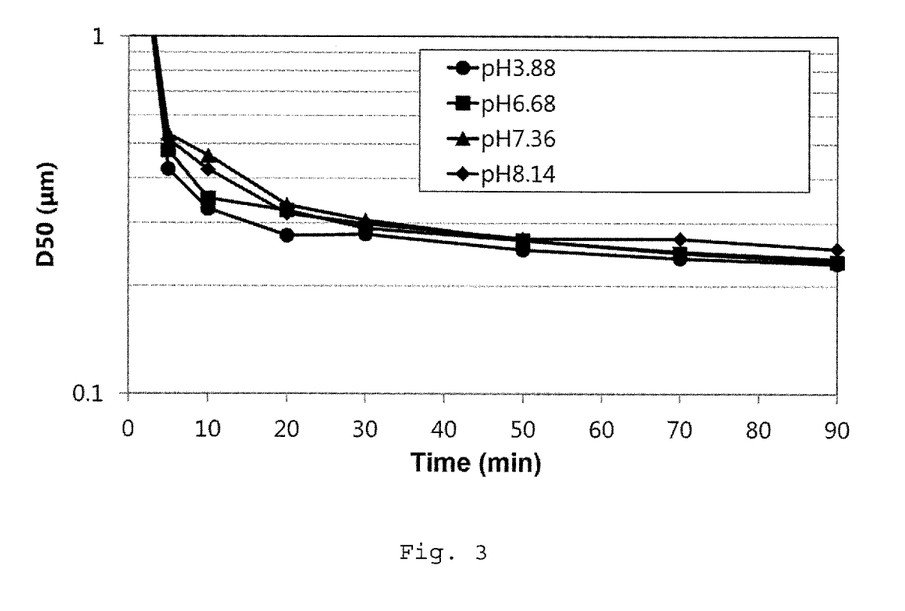
FIG. 3 shows the effect of pH on the grinding efficiency in Test Example 2. The horizontal axis indicates the grinding time. The vertical axis indicates the particle size (D50) of the drug fine particles after the grinding.

As shown in FIG. 3, no significant effect of pH was observed on the grinding efficiency.

Test Example 3: Effect of pH on the Contamination

For each of the slurries prepared in Test Example 2 having different pH (pH 3.88, 6.68, 7.36 and 8.14), the grinding process by the bead mill and sampling at a predetermined time point were carried out as described in Test Example 2. Each sample was dissolved as described in Example 1, and the amounts of zirconium, yttrium and aluminum in the sample were measured using an inductively coupled plasma mass spectrometer. The results are shown in FIG. 4.

Figure 4:
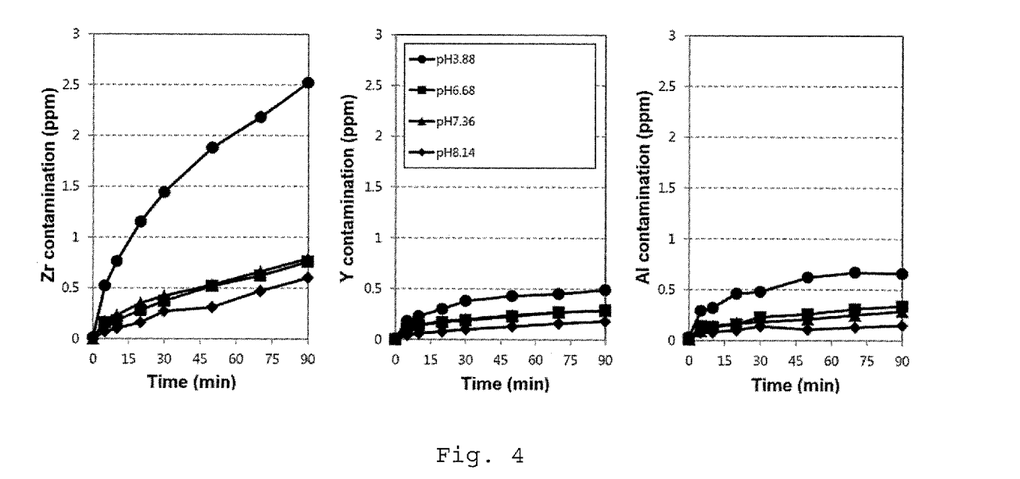
FIG. 4 shows the effect of pH on the contamination in Test Example 3. The horizontal axis indicates the grinding time. The vertical axis indicates the amount of the elements derived from the beads in the sample (zirconia (Zr), yttrium (Y) and aluminum (Al)).

As shown in FIG. 4, when the grinding process was carried out with adjusting the pH of the slurry to 6.68 to 8.14, the contamination was reduced for each ingredients derived from beads (zirconium, yttrium, aluminum).

Test Example 4

100 g of the slurry (pH 3.88 and pH 7.36) prepared in Test Example 2 and 217.3 g (filling ratio 70%) of YTZ ball (zirconia beads manufactured by Nikkato Corporation) were charged into Dyno-mill Research Lab (manufactured by WAB) and subjected to grinding process by the bead mill (disc peripheral speed: 4 m/s) or left to stand as they were without grinding process (disc peripheral speed: 0 m/s).

Sampling was carried out at a predetermined time point, and the sample after the grinding process was dissolved as described in Example 1. The amounts of zirconium, yttrium and zirconium in the sample were measured using an inductively coupled plasma mass spectrometer. The results are shown in FIG. 5.

Figure 5:
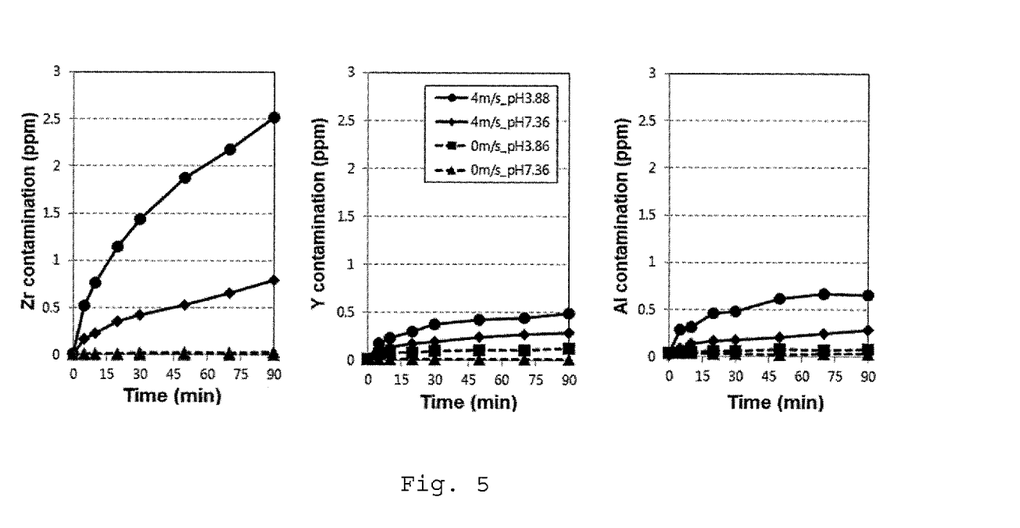
FIG. 5 shows the effect of the grinding process and pH on the contamination in Test Example 4. The horizontal axis indicates the grinding time. The vertical axis indicates the amount of the elements derived from the beads in the sample (zirconia (Zr), yttrium (Y) and aluminum (Al)).

As shown in FIG. 5, when the grinding process was carried out (disc peripheral speed: 4 m/s), the contamination by the ingredients derived from beads was increased. It is considered that this was due to the wear of the grinding medium (beads) during the grinding process. However, the contamination caused by the grinding process was decreased by adjusting the pH of the slurry (pH 7.36).

The invention claimed is:

1. A method for the production of fine particles via a grinding process using a bead mill,
wherein the method comprises:
   a) a step of preparing a slurry comprising a material to be ground and a dispersion medium,
   b) a step of adjusting the pH of the slurry prepared in the step a) to 6.5 to 9, and
   c) a step of agitating the slurry prepared in the step b) and beads in the bead mill; or
wherein the method comprises:
   a') a step of preparing a slurry comprising a material to be ground, beads and a dispersion medium,
   b') a step of adjusting the pH of the slurry prepared in the step a') to 6.5 to 9, and
   c') a step of agitating the slurry prepared in the step b') in the bead mill;
   wherein the material to be ground is a pharmaceutical compound, wherein impurities caused by the grinding process are derived from the beads and/or the bead mill, and wherein an amount of the impurities is less than 50 ppm with respect to the weight of the material to be ground.

2. The method according to claim 1, wherein the dispersion medium comprises at least one selected from the group consisting of sodium linear alkylbenzene sulfonate, monoalkyl phosphate, sodium lauryl sulfate, cellulose polymer and vinyl polymer.

3. The method according to claim 1, wherein the dispersion medium comprises polyvinylpyrrolidone.

4. The method according to claim 1, wherein the dispersion medium comprises sodium lauryl sulfate.

5. The method according to claim 1, wherein the dispersion medium comprises polyvinylpyrrolidone and sodium lauryl sulfate.

6. The method according to claim 1, wherein the step b) of adjusting the pH of the slurry prepared in the step a) to 6.5 to 9 comprises adding an acidic substance or a basic substance to the slurry, or
   wherein the step b') of adjusting the pH of the slurry prepared in the step a') to 6.5 to 9 comprises adding an acidic substance or a basic substance to the slurry.

7. The method according to claim 1, wherein the beads are zirconia beads.

8. The method according to claim 1, wherein the beads comprise zirconium, yttrium and aluminum.

9. The method according to claim 1, wherein the impurities are at least one selected from the group consisting of zirconium, yttrium and aluminum.

10. The production method according to claim 1, wherein the fine particles are microparticles.

11. The production method according to claim 1, wherein the fine particles are nanoparticles.

12. Fine particles obtained by the method according to claim 1.

13. The fine particles according to claim 12, which are microparticles.

14. The fine particles according to claim 12, which are nanoparticles.

15. The fine particles according to claim 12, wherein the fine particles comprise at least one kind of impurities selected from the group consisting of zirconium, yttrium and aluminum, and the amount of the impurities is 0.0001 ppm or more and less than 50 ppm.

16. A pharmaceutical composition comprising the fine particles according to claim 12.

17. A method for reducing impurities caused by a grinding process using a bead mill,
wherein the method comprises:
   a) a step of preparing a slurry comprising a material to be ground and a dispersion medium,
   b) a step of adjusting the pH of the slurry prepared in the step a) to 6.5 to 9, and
   c) a step of agitating the slurry prepared in the step b) and beads in the bead mill; or
wherein the method comprises:
   a') a step of preparing a slurry comprising a material to be ground, beads and a dispersion medium,
   b') a step of adjusting the pH of the slurry prepared in the step a') to 6.5 to 9, and
   c') a step of agitating the slurry prepared in the step b') in the bead mill;
   wherein the material to be ground is a pharmaceutical compound, wherein impurities caused by the grinding process are derived from the beads and/or the bead mill, and wherein an amount of the impurities is less than 50 ppm with respect to the weight of the material to be ground.

* * * * *